United States Patent [19]

Dickhudt et al.

[11] 4,414,986

[45] Nov. 15, 1983

[54] BIOMEDICAL STIMULATION LEAD

[75] Inventors: Eugene A. Dickhudt; Roger A. Paulson, both of New Brighton, Minn.

[73] Assignee: Medtronic, Inc., Minneapolis, Minn.

[21] Appl. No.: 344,124

[22] Filed: Jan. 29, 1982

[51] Int. Cl.$^3$ .............................................. A61N 1/04

[52] U.S. Cl. .................................... 128/785; 128/786

[58] Field of Search ............................... 128/784–786, 128/419 P

[56] References Cited

U.S. PATENT DOCUMENTS

| | | | |
|---|---|---|---|
| 3,835,864 | 9/1974 | Rasor et al. | 128/785 |
| 3,952,742 | 4/1976 | Taylor | 128/419 P X |
| 4,026,303 | 5/1977 | Babotai | 128/785 |
| 4,033,357 | 7/1977 | Helland et al. | 128/785 |
| 4,154,247 | 5/1979 | O'Neill | 128/419 P |
| 4,285,347 | 8/1981 | Hess | 128/785 |
| 4,301,815 | 11/1981 | Doring | 128/785 |
| 4,360,031 | 11/1982 | White | 128/786 |
| 4,379,462 | 4/1983 | Borkan et al. | 128/786 |

FOREIGN PATENT DOCUMENTS

| | | | |
|---|---|---|---|
| 9732 | 4/1980 | European Pat. Off. | 128/785 |
| 2929189 | 1/1980 | Fed. Rep. of Germany | 128/784 |
| WO80/00170 | 12/1980 | PCT Int'l Appl. | 128/786 |

OTHER PUBLICATIONS

Pisces–Sigma ®, An Epidural Spinal Cord Stimulation System Featuring a New Concept in Lead Design, Medtronic Neuro, Medtronic, Inc., Neuro Division, 3055 Old Highway Eight, P.O. Box 1453, Minneapolis, MN 55440- ©Oct. 1980, Medtronic, Inc.

*Primary Examiner*—Lee S. Cohen

*Attorney, Agent, or Firm*—Robert J. Klepinski; John L. Rooney; Joseph F. Breimayer

[57] ABSTRACT

A biomedical stimulation lead wherein the lead body is preformed into a helical configuration to assist in anchoring the lead. The lead includes a non-conducting member extending forward of the lead electrode along the axis of the lead body, and tines extending perpendicularly from the member. The tines are flat in a plane perpendicular to the axis of the lead.

10 Claims, 3 Drawing Figures

10 11 15 12 30 31 19

BIOMEDICAL STIMULATION LEAD

BACKGROUND OF THE INVENTION

1. Field of the Invention

This invention in general relates to the field of leads for the electrical stimulation of living tissue, and more particularly, concerns a lead having improved means for anchoring the lead which result in a lead which is unusually resistent to dislodgment when placed within the epidural space.

2. Description of the Prior Art

Electrical stimulation of the body is an increasingly important medical procedure. In particular, electrical stimulation of the spinal cord has proven to be effective in relieving chronic pain. In this stimulation context, a lead is introduced into the epidural space which surrounds the spinal cord. With the patient under local anesthesia at the point of insertion, the lead is maneuvered by the surgeon until the position is obtained in which the lead provides the maximum relief to the particular patient. A problem encountered in many stimulating contacts and, in particular, in the context of stimulation of the spinal cord within the epidural space, is the dislodgment of the electrode after insertion. This problem arises from a number of factors, including: the lack of structure within the epidural space which might engage the lead and prevent it from moving; the fact that the dura and surrounding tissue of the spinal cord are extremely sensitive and considerable pain and possible permanent damage can result if this region is traumatized, making gross anchoring techniques such as penetration or fixation to the tissue are impossible; and the fact that 10 cm to 20 cm of lead may extend into the epidural space from the point of entry (at which point the lead can be firmly anchored just outside the epidural space). Dislodgment of the stimulation electrode tip after insertion may substantially lessen the relief the treatment provides, or make the treatment completely ineffective.

U.S. Pat. No. 4,044,774 issued Aug. 30, 1977 on an invention of Terry Corbin and Duane Zykovitz extensively discusses the techniques of spinal cord stimulation in the epidural space and the related problem of lead placement. This patent relates particularly to the structure within the lead body itself, and it does not appear to disclose anchoring apparatus external of the lead body.

U.S. Pat. No. 3,902,501 for an endocardial electrode issued Sept. 2, 1975 on an invention of Paul Citron and Eugene Dickhudt, U.S. Pat. No. 3,939,843 for a transvenous electrode, issued Feb. 24, 1976, on an invention of Nicholas P. D. Smyth, and U.S. Pat. No. 4,236,529 for a tined lead issued Dec. 2, 1980 on an alleged invention of Richard L. Little all relate to leads employing tines for anchoring an electrical stimulation lead. U.S. Pat. No. 4,236,529 cited above also discloses flattened tines; however, the tines are flattened in a direction parallel to the axis of the lead body, and the patent discloses that the purpose of the flattening is to make the tines thinner so that they are more flexible about the lead body axis. The above patents all disclose that the tines engage trabeculae within the body organ such as the heart, to provide lead anchoring. Since the epidural space does not contain trabeculae or other similar tissue, extension of the tined lead to the epidural space is not evident from these patents. U.S. patent application Ser. No. 926,100 filed July 19, 1978 on an invention of Alfred A. Iversen for a body stimulation lead discloses a body stimulation lead for use in the epidural space which employs a plurality of lobes preformed in the lead body to assist in maintaining the position of the electrode. U.S. Pat. No. 4,285,347 discloses another electrode employing lobes for anchoring an electrode in the epidural space. U.S. Pat. Nos. 3,866,615 and 4,154,247 disclose electrodes having lobes which are employed for anchoring electrodes in the heart.

SUMMARY OF THE INVENTION

It is an object of the invention to provide a biomedical stimulation lead having improved anchoring characteristics without traumatizing the surrounding body tissue.

It is also an object of the invention to provide a stimulation lead which is particularly well suited for stable placement within the epidural space.

It is a further object of the invention to provide a stimulation lead which particularly resists movement in a direction parallel to the axis of the lead.

In addition, it is an object of the invention to provide a stimulation lead which absorbs various shocks which might otherwise tend to move the lead, and at the same time resists movement as described above.

It is a further object of the invention to provide a lead which satisfies the above objects and at the same time can be inserted into the epidural space using conventional techniques.

The invention provides a biomedical stimulation lead for implantation in a living body comprising an exposed electrode and a lead body which includes a conductor connected to the electrode and a casing forming the external portion of the lead body, the casing being of a pliable material generally inert to body fluids. In one aspect of the invention, the lead body is preformed into a helical configuration over a portion of its length. In another aspect of the invention there are tines extending substantially perpendicularly from the lead body, which tines are substantially flat in the plane perpendicular to the axis of the lead body. In a third aspect of the invention there is a pliable non-conducting member extending substantially along the axis of the lead body at a location forward of the electrode and pliable tine means extending substantially perpendicularly from the extension. The invention also includes various combinations of the above three aspects. It has been found that the invention as thus described provides a lead with greatly improved stability and freedom from dislodgment within the epidural space. Numerous other features, objects and advantages of the invention will become apparent from the following detailed description when read in conjunction with the accompanying drawings.

DESCRIPTION OF THE PREFERRED EMBODIMENT

Figure 2:
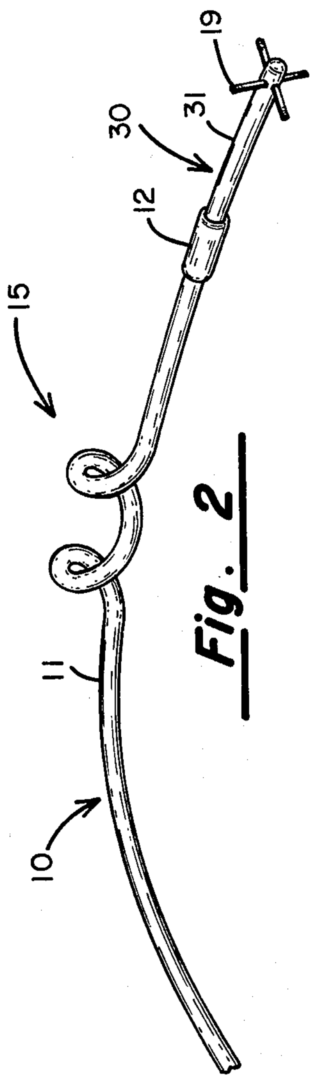
FIG. 2 is a perspective view of a preferred embodiment of a lead according to the present invention.

A lead 10 according to the invention is shown in FIG. 2. Lead 10 includes a lead body 11 and an exposed electrode 12. The principle features of the present invention comprise a helical configuration of the lead body shown at 15 and tines 19 which resist motion of the lead through the epidural space, thus preventing lead dislodgment. Another feature of the invention is lead body extension member 31 which spaces tines 19 from electrode 12.

The internal structure of the lead 10 is conventional. In order to fully understand the invention, this internal structure will be briefly described with respect to the prior art epidural lead shown in FIG. 1. The prior art lead 20 includes a lead body 21 and an electrode 22. The lead body 21 includes conductor 23 and casing 24 which encloses conductor 23 and forms the external portion of the lead (except in the area of exposed electrode 22). Generally, conductor 23 is in the form of a helical coil having an opening or lumen 25 passing down the central axis of the coil. A stylet 27 having a stylet handle 28 may be inserted into the lumen so that it extends axially along the length of the lead body 21 in order to stiffen the lead while it is being inserted. After the lead is inserted, the stylet 27 is removed. In the typical lead, end 29 is adapted to be connected to a source of an electronic pulse, such as a pulse generator, a receiver or a lead extension (not shown) and the electrode 22 is located at or near the other end of the lead. We shall hereinafter refer to the end 29 of the lead which is connected to the pulse source as the rearward end of the lead and the opposite end identifiable by the electrode 22 as the forward end of the lead.

We shall now describe the principle features of the invention more fully in reference to FIG. 2. Shown at 15, in the preferred embodiment of the invention, a portion of the lead body is formed into a helix generally coaxial with lead body 11. As shown, the helix has two full turns with the length of the two turns preferably approximately 1 in. and the diameter of the helix being preferably about 0.2 in. However, the invention contemplates any combination of helix diameter, number of turns, and spacing which provides a helix that will fit within the epidural space without creating undesirable pressures on the dura and other structures in the region. Preferably the helix is a lefthand helix looking from the forward end of the lead toward the rear. The casing of the lead body 10 is preferably formed of polyurethane and the helix is formed by molding the polyurethane in a heated press. Other material such as silicone rubber and other methods of forming a helix may be used.

Figure 3:
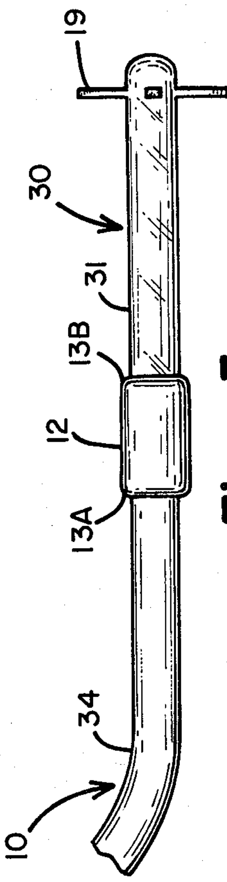
FIG. 3 is a side view of the forward portion of the lead shown in FIG. 2.

The preferred embodiment of the invention also includes the tined piece part 30. This piece part 30, which perhaps best can be seen in FIG. 3, consists of a hollow cylindrical extension 31, and the tines 19. The entire piece part 30 is molded of polyurethane in a heat press. Piece part 30 is connected to lead body 10 by electrode 12. Electrode 12 is swaged onto the lead body 10 and piece part 30 so that the ends 13*a* and 13*b* pierce through casing 34 and hollow cylindrical extension 31 of the piece part 30 respectively to hold them together. The method of manufacturing using the electrode to securely fasten the piece part 30 to lead body 10 and, at the same time, make electrical contact to conductor 23 is more fully described in co-pending U.S. patent application Ser. No. 344,125 (entitled Biomedical Lead With Ring Electrode and Method of Making Same by Eugene A. Dickhudt) and will not be discussed further here.

The principle features of the piece part 30 of concern for purposes of the present invention are extension 31 and tines 19. Extension 31 extends substantially parallel to the axis of said lead body 34. Tines 19 are preferably formed in the form of small rectangular plank-like members about 0.08 in. long, 0.01 in thick and 0.012 in. in width, with the 0.012 in. width preferably being aligned in a plane substantially perpendicular to the axis of the lead body 10 and extension 31, so that they are substantially flat in this plane. Preferably the tines extend substantially perpendicular from the surface of extension 31. Substantially here means that the extension is sufficiently parallel and the tines are sufficiently flat and sufficiently perpendicular so that the major portion of the tine surface area opposes motion through the epidural space in a direction parallel to the axis of the lead. Extension member 31 as shown is preferably of a length which places the tines 19 about 0.3 in. from the end 13*b* of electrode 12. Hollow cylindrical extension 31 is preferably about 0.04 in. in diameter which is the same as the diameter of lead body 10. The invention contemplates that any size and shape of tines and any dimensions of extension 31 may be used that are consistent with: the tines and extensions being able to be inserted through a Touhy needle; with the tines serving to impede motion in the axial direction; and with the tines not being so long as to create undesirable pressure on the dura and other structures within the epidural space.

In the preferred embodiment, the spacing of helix 15, electrode 12 and tines 19 are such that electrode 12 falls approximately $\frac{1}{4}$ to $\frac{1}{2}$ of the distance from tines 19 to helix 15. The tines 19 and helix 15 are close enough to the electrode to provide a significant stabilization effect, and not so close that fibrosis or other tissue buildup about the tines and helix will interfere with the electrical stimulation at the electrode. The helix, extension and tines as thus described cooperate to provide an electrode which is significantly more stable in the period immediately after implant than other leads previously designed for the epidural space. Moreover, after implant, the body creates fibrosis and other tissue buildup around tines 19 which serves to firmly hold them in place. Thus, the preferred embodiment of the invention provides an electrode which is secured between two fixation points.

Helix 15 serves a dual purpose in the invention. It not only serves as a fixation point as described above, but also serves as a means for absorbing shocks supplied to the lead body. The helical turns expand and contract in the case of sudden forces applied to lead body 10 which tends to isolate electrode 12 from these forces. The drag provided by flattened tines 19 in the epidural space also tends to cooperate with the extendability of the helix 15 to help isolate electrode 12 from sudden movements or shocks to lead body 10. It is noted that the helix effectively provides significantly more surface opposing motion in a direction along the axis of the lead than other prior art lead anchoring structures. The helix and tines also stabilize the lead in the directions prependicular to the axis.

Figure 1:
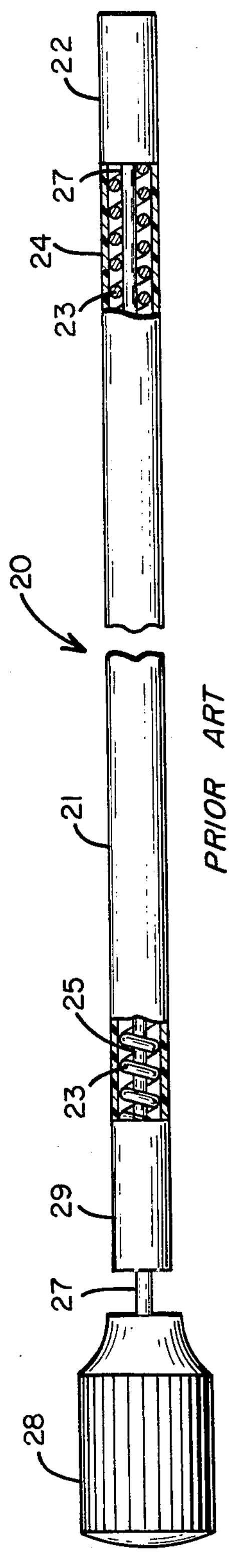
FIG. 1 is a partially cutaway view of a prior art lead, showing the internal structure of the lead body and the placement and use of a stylet.

Another feature of the invention is that the entire lead can be inserted into the epidural space through conventional methods. Prior to insertion a stylet such as shown at 27 and 28 in FIG. 1 is inserted into lead body 10 which straightens the turns of helix 15. The entire lead may then be inserted into the body in the conventional manner through a Touhy needle, with the tines flattening down against extension 31 upon insertion into the needle. The flattening of the tines serves to make entry into the needle easier. The tines 19 re-extend themselves after passing through the needle. After removal of the stylet, helix 15 reforms to cooperate with the tines in stabilizing the lead.

The invention comtemplates that the tines 19 may be used alone as a stabilization means (without the helix) or in combination with other stabilization means. Previous to the present invention, it was not believed that tines would be effective in the epidural space, since in all previous applications of tines trabeculae or other natural body tissues were always available to interact with the tines. Further, it was believed that the tines may be too traumatic for use in the epidural space. Surprisingly, the tines have proven to be an effective anchor without causing trauma. The invention also contemplates that the helix 15 may be used alone (without the tines) or in combination with other stabilization means. The invention represents the first time a helix formed in a lead body has been used to anchor any stimulation lead. It has been found that the helix provides surprisingly increased anchoring force than other prior art lead anchoring structures. In addition, the helix has the advantage that almost any number of turns can be formed without greatly affecting the ability of the surgeon to collapse the turns by insertion of the stylet and to pass the lead through the Touhy needle.

There has been described a novel biomedical stimulation lead that provides for greatly improved electrode stability, and at the same time can be inserted into the epidural space by conventional means. While the invention has been described in connection with three particular embodiments, one skilled in the art will appreciate that numerous other embodiments and departures from the embodiment shown may be made without departing from the inventive concepts. For example, a wide variety of materials may be used for forming the casing 34 of the lead body, the extension 31, and the tines 19, so long as the material is pliable and is resistent to body fluids. Clearly, now that the invention has been described, a wide variety of dimensions for the elements such as the helix 15, the extension 31 and the tines 19 may be chosen by those skilled in the art to arrive at the desired characteristics as described or some other combination of tines with other structures may be used. In addition, other features may be added to the lead while still employing the inventive elements. It is therefore to be understood that, within the scope of the appended claims, the invention may be practised other than as it has been specifically described.

What is claimed is:

1. A biomedical stimulation lead for insertion in an epidural space comprising:

a lead body, having a distal end and a proximal end, including a conductor and an external casing made of pliable material generally inert to body fluids, the casing enclosing the conductor;

attachment means mounted adjacent the distal end of the lead body for attaching by fibrosis within the epidural space;

an exposed electrode mounted on the lead body spaced proximally away from the attachment means for stimulating within the epidural space, the electrode being conductively connected to the conductor; and wherein the lead body is formed in a helix at a location proximally spaced from the electrode, the helix being generally coaxial with the lead body for bearing outward to hold the lead body within its position in the epidural space and for absorbing intermittent longitudinal pressure on the lead body in a proximal direction.

2. The lead of claim 1 wherein the attachment means comprises:

a plurality of pliable tines mounted on the lead body.

3. The lead of claim 2 wherein the tines are substantially perpendicular to a longitudinal axis of the lead body.

4. The lead of claim 3 wherein the tines are rectangular plank-like members.

5. The lead of claim 4 wherein the tines are spaced proximally approximately 0.3 inches from the distal end of the lead body.

6. The lead of claim 1, wherein the helix includes at least two full turns and has an outside diameter of approximately 0.2 inches.

7. The lead of claim 6 wherein the helix is a lefthand helix when viewed from the distal end in the proximal direction.

8. A biomedical stimulation lead for insertion in an elongated narrow body cavity comprising:

a lead body, having a distal end and a proximal end, including a conductor and an external casing made of pliable material generally inert to body fluids, the casing enclosing the conductor;

a plurality of pliable tines mounted on the lead body adjacent the distal end of the lead body, generally perpendicular to a longitudinal axis of the lead body, for attachment by fibrosis within the body cavity;

a helix formed in the lead body at a first location spaced away from the tines, the helix being generally coaxial with the longitudinal axis of the lead body and sized for bearing outward to hold its position in the body cavity and for absorbing intermittent longitudinal pressure on the lead body in a proximal direction; and a stimulation electrode mounted on the lead body at a second location between the tines and the helix and conductively connected to the conductor.

9. The lead of claim 8 wherein:

the tines are rectangular plank-like members mounted approximately 0.3 inches from the distal end of the lead body.

10. The lead of claim 8 wherein:

the helix includes at least two full turns and has an outside diameter of approximately 0.2 inches.

* * * * *